United States Patent [19]

Gupton

[11] 4,367,736
[45] Jan. 11, 1983

[54] SYSTEM FOR DETECTING BUBBLE FORMATION IN CLEAR AND OPAQUE FLUIDS

[75] Inventor: John E. Gupton, Vernon Hills, Ill.

[73] Assignee: Baxter Travenol Laboratories, Inc., Deerfield, Ill.

[21] Appl. No.: 181,063

[22] Filed: Aug. 25, 1980

[51] Int. Cl.³ .............................................. A61M 5/14
[52] U.S. Cl. ...................... 128/214 E; 128/DIG. 13; 340/632
[58] Field of Search .................. 128/DIG. 13, 214 E; 340/632; 73/19; 356/39

[56] References Cited

U.S. PATENT DOCUMENTS

| | | | |
|---|---|---|---|
| 2,835,252 | 5/1958 | Mauchel | 356/39 X |
| 3,812,482 | 5/1974 | Clark | 128/214 E X |
| 3,935,876 | 2/1976 | Massie et al. | 128/DIG. 13 X |
| 4,114,144 | 9/1978 | Hyman | 128/DIG. 13 X |
| 4,280,495 | 7/1981 | Lampert | 128/214 E |

Primary Examiner—Kyle L. Howell
Assistant Examiner—John C. Hanley
Attorney, Agent, or Firm—Paul C. Flattery; John P. Kirby, Jr.; Eugene M. Cummings

[57] ABSTRACT

A system for use in flow metering apparatus for detecting bubble formation in both clear and opaque fluids in an administration set includes a light source and a light detector positioned on opposite sides of a transparent tubing segment of the administration set such that light transmitted through the tubing to the detector is dependent on the presence or absence of fluid in the tubing. With clear fluid present, a first comparator in the system interrupts operation of the metering apparatus when the light detector output falls below a predetermined minimum level. With opaque fluid present, a second comparator interrupts operation of the apparatus when the light detector output rises above a predetermined maximum level. The detection system is automatically conditioned to either clear or opaque operating modes without input from the operator, and incorporates protection circuitry for interrupting operation of the metering apparatus in the event of failure of either the light source or the light detector.

16 Claims, 9 Drawing Figures

FIG.7

SYSTEM FOR DETECTING BUBBLE FORMATION IN CLEAR AND OPAQUE FLUIDS

BACKGROUND OF THE INVENTION

The present invention relates generally to fluid infusion systems, and more particularly to an improved system for detecting the formation of bubbles in such systems.

The infusion of fluids such as parenteral fluids into the human body is usually accomplished by means of a one-use disposable administration set which establishes a flow path between a reservoir of fluid to be infused and an injection site. Where the rate of administration is critical, such flow systems may include metering apparatus to establish a user-selected flow rate. Such metering is typically of either the cassette type, wherein an externally driven pump element is integrally included in the administration set, or of the peristaltic-type, wherein a section of tubing of the administration set is repetitively compressing and expanded. An example of the latter type of metering apparatus as described in U.S. Pat. No. 4,155,362, is marketed as the Model 2M8014 infusion pump by Baxter Travenol Laboratories, Inc., of Deerfield, Ill.

One problem which arises with the use of administration sets is that bubbles of air or gas contained in the sets may be inadvertantly infused along with the fluid, an occurrence which may be harmful or even fatal to the patient under certain circumstances. Bubbles may arise in the system as a result of improper set-up of the administration set or inadvertant depletion of the fluid source, or as a result of dissolved gases in the fluid being released as the fluid is subjected to pressure and/or temperature changes by the metering apparatus.

To prevent air or gas from being infused it has become common practice to provide a bubble detection system in the apparatus to automatically stop the apparatus should gas bubbles be detected downline of the metering apparatus. Such detection systems typically employ a light source and a light detector positioned on opposite sides of the administration set tubing to monitor the level of light transmitted through the tubing. Operation of the metering apparatus is interrupted and an alarm is sounded when the transmitted light level falls below a predetermined level.

One shortcoming of such bubble detection systems has been their inability to monitor both opaque fluids, such as blood components, and transparent fluids, such as medicinal solutions, without user-initiated conditioning to an appropriate operating mode. Not only did the necessity for such conditioning in prior art detection systems unduly complicate the set-up procedure, but it also introduced the possibility of inadequate protection should the systems be inadvertently conditioned for operation in the wrong mode.

The present invention is directed to a bubble detection system which is automatically conditioned to an appropriate operating mode for use with transparent and opaque fluids.

Accordingly, it is a general object of the present invention to provide a new and improved bubble detection system.

It is another object of the present invention to provide a new and improved bubble detection system operable in conjunction with both transparent and opaque fluids in a fluid infusion system.

SUMMARY OF THE INVENTION

The invention is directed, in a flow metering apparatus for controlling the flow of fluid through an administration set of the type having transparent tubing, to a bubble detection system comprising a light source arranged at one side of the tubing, and a light detector generally arranged at the opposite side of the tubing and defining in conjunction with the light source a light path through the tubing. The light detector generates an output signal in response to the intensity of light from the light source incident thereon, the intensity of the incident light increasing in the presence of fluid within the lumen of the tubing as a result of the focusing effect thereof, and decreasing in the presence of an opaque fluid within the lumen. Detector circuit means responsive to the output signal are provided for interrupting operation of the flow metering apparatus upon the intensity of the light incident on the light detector falling below a predetermined minimum level in the presence of transparent fluid in the lumen, and for interrupting operation upon the intensity of the light incident on the light detector rising above a predetermined maximum level in the presence of opaque fluid in the lumen.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, and the several figures of which like reference numerals identify like elements, and in which:

DESCRIPTION OF THE PREFERRED EMBODIMENT

Figure 1:
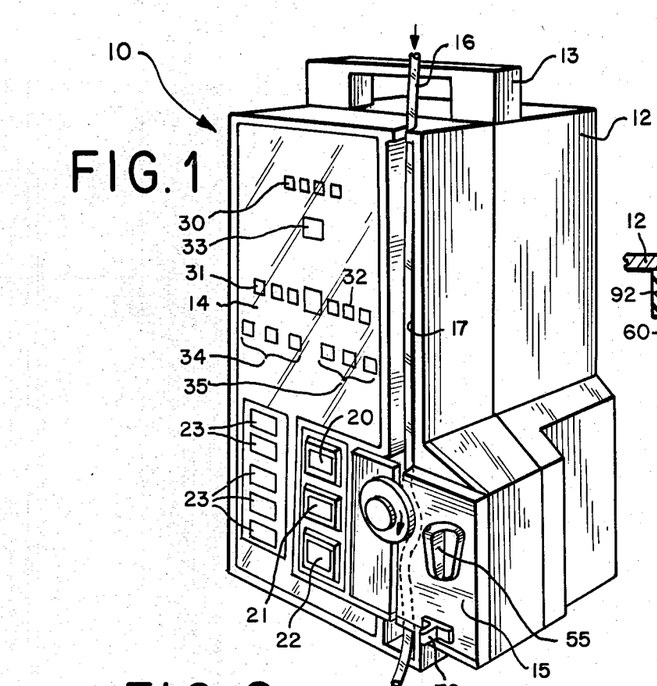
FIG. 1 is a perspective view of a metering apparatus incorporating a bubble detection system constructed in accordance with the invention.

Referring to the Figures, and particularly to FIG. 1, a peristaltic-type flow metering apparatus 10 for use in conjunction with an administration set for controlling the flow of fluid into a vein or artery includes a generally rectangular housing 12 having a handle 13 at one end for convenient carrying. The front surface of the housing includes a control panel 14 which allows the operator to control and monitor the operation of the metering apparatus, and a peristaltic-type flow metering head 15 for compressing a section of tubing 16 of the administration set to effect control of fluid flow therein. A channel 17 is provided above metering head 15 for maintaining a portion of the tubing segment in convenient view of the operator so that flow irregularities can be more readily observed.

The administration set, of which tubing segment 16 is a part, and which may be conventional in design and construction, is preferably formed of a plastic material such as vinyl and packaged in a sterile and non-pyrogenic condition. To avoid the danger of contamination, the administration set is normally utilized for one application only, and is disposed of after a single use.

The operating mode of metering apparatus 10 is controlled by means of a push button STOP switch 20, a push button START switch 21, and a push button power ON-OFF switch 22. Each of these push button switches includes an internal indicator lamp which provides a positive indication of the operating mode of the apparatus. Various abnormal operating conditions are annunciated by means of indicator lights 23 contained on the control panel to the left (as viewed in FIG. 1) of the mode control push buttons.

Control panel 14 further includes a digital display 30 of volume infused, a digital display 31 of volume to be infused, and a digital display 32 of fluid flow rate. The volume displayed by display 30 is the volume of fluid actually infused, and can be reset to zero by the operator by means of a push button RESET switch 33. The volume to be infused displayed by display 31 is preset by the operator by means of a set of push button switches 34 to indicate a desired volume of fluid to be infused. Similarly, the infusion rate displayed by display 32 is preset by the operator by means of a second set of push button switches 35 to indicate the rate at which infusion is to take place.

The operation of the various indicators, control switches and other features of metering apparatus 10 is described in detail in the copending applications of Thurman S. Jess and Norm Shim, Ser. No. 856,863; Norm Shim, Ser. No. 857,018; Norm Shim and Vincent L. Knigge, Ser. No. 856,927; and Thurman S. Jess, Ser. No. 856,926; all filed Dec. 2, 1977.

Figure 2:
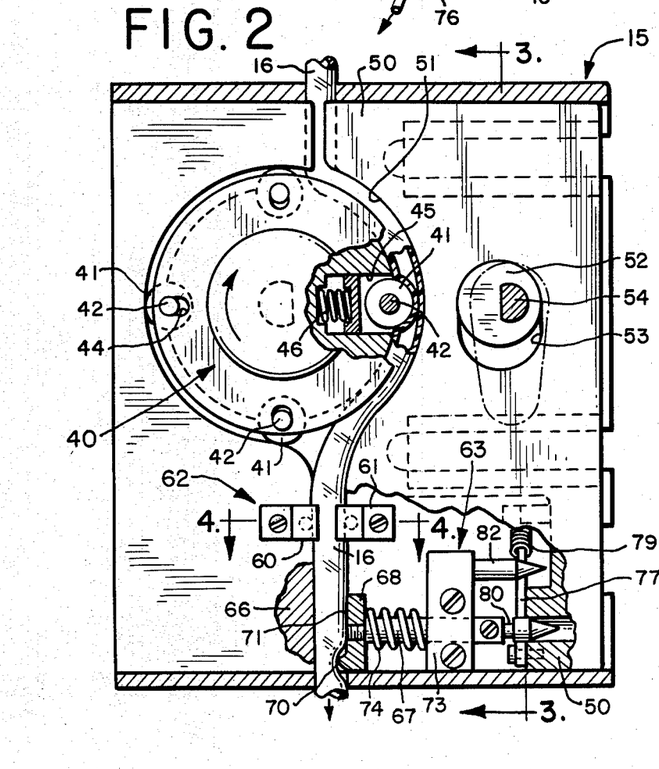
FIG. 2 is an enlarged front elevational view of the metering station of the flow metering apparatus partially in section and partially broken away to illustrate the operation thereof.
Figure 3:
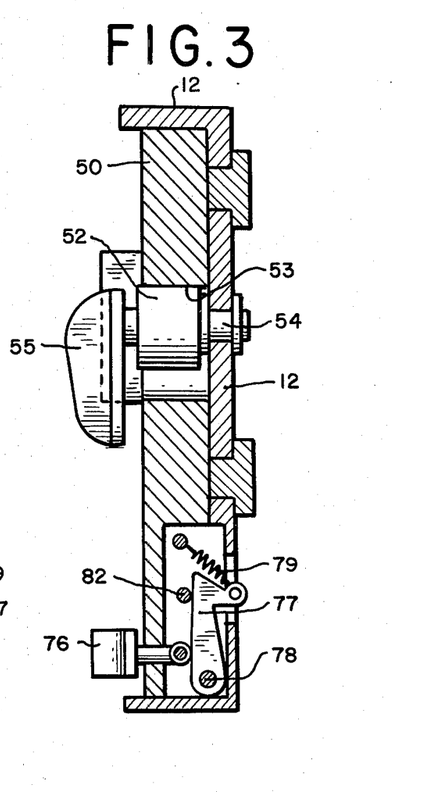
FIG. 3 is a cross-sectional view of the metering station taken along line 3—3 of FIG. 2.

Referring to FIGS. 2 and 3, the peristaltic metering head 15 includes a rotor 40 having four pressure rollers 41 disposed in equi-spaced relation about its circumference. The rollers are each mounted on a shaft 42 for free rotation, and the shafts are carried on carriages and constrained to radial movement by respective radial slots 44. Each carriage is mounted for reciprocation within a radial recess 45 and spring loaded radially outwardly by a helical spring 46 disposed within the recess.

The metering pump also includes a pressure plate 50 having an arcuate working surface 51 which substantially corresponds in shape to the circumference of rotor 40. This working surface brings tubing 16 into compressive engagement with rollers 41 around at least a portion of the rotor circumference corresponding to the spacing between adjacent rollers. The pressure plate may be reciprocated toward and away from rotor 40 to facilitate installation and removal of tubing 16 by rotation of an eccentric cam 52, which is constrained to operate within a vertical slot 53 provided on the pressure plate. Rotation of the cam is accomplished by a shaft 54 and a user-actuable lever 55 operatively connected to the cam. When the lever 55 is in its vertical position, as shown in FIG. 3, the pressure plate is moved sufficiently close to the rotor circumference to cause tubing 16 to be completely occluded by one of the pressure rollers 41.

After passing through metering station 15, tubing 16 extends between a light source 60 and a light detector 61, which together comprise a fluid absence monitoring head 62. This head, combined with associated control circuitry, forms a bubble detection system which interrupts operation of the metering apparatus and alerts the operator upon formation of a bubble in the tubing.

The tubing next passes through a flow restriction station 63. This station includes a pressure block 66 and a reciprocatively mounted plunger 67 biased against the sidewall of tubing segment 16. The end of plunger 67 which engages the tubing segment includes a generally L-shaped head portion 68 having a wedge-shaped working surface 70 which occludes the tubing and a generally flat control surface 71 which responds to fluid pressure changes. Plunger 67 is slidably received within a mounting block 73, and extends through the center of a helical compression spring 74 which biases head 68 into engagement with the tubing. The occlusion of the tubing by the flow restriction station increases the pressure of the fluid in the tubing at the point of engagement of the rollers 41 of rotor 40 to assist in restoration of the tubing following compression by the pressure rollers for improved metering accuracy.

Plunger 67 can be opened to facilitate loading or unloading of tubing 16 by means of a lever 76. The plunger is locked open by means of a latch member 77 which is pivotally mounted at 78 to pressure plate 50 and biased by a helical spring 79 for operation within a plane perpendicular to the plunger. Latch member 77 is received in a slot 80 on the plunger when the plunger is moved to its full open position.

To insure that plunger 67 will be released when pressure plate 50 is subsequently closed, an actuator pin 82 having a tapered end surface displaces latch member 77 from slot 80 when the pressure plate is returned to its closed position by rotation of knob 55. This prevents inadvertent operation of the system without the back pressure and gravity flow protection provided by the plunger. Also, when the pressure plate is opened, the displacement of latch member 77 prevents the plunger from being latched open.

Figure 4:
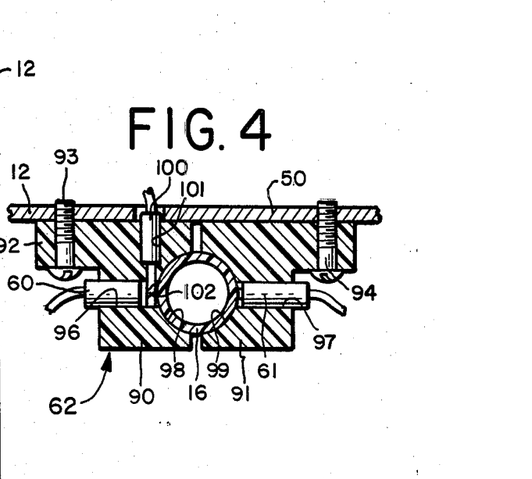
FIG. 4 is an enlarged cross-sectional view of the flow monitoring head of the metering station taken along line 4—4 of FIG. 2.

Referring to FIG. 4, flow monitoring head 62 is seen to comprise first and second form members 90 and 91 disposed on opposite sides of tubing segment 16. The first form member 90 is secured to housing 12 by a bolt 93 extending through a flange portion 92. Similarly, the second form member 91 is secured to the slidable pressure plate 50 by means of a bolt 94 extending through a flange portion 95 of the base member.

To provide mounting means for light source 60, the first form member 90 is provided with a bore 96 perpendicularly aligned to the axis of tubing 16. To provide a receptacle for photodetector 61, form member 91 is similarly provided with a perpendicularly aligned bore 97. Bores 96 and 97 are each dimensioned with an inside diameter just slightly larger than the outside diameter of light source 96 and photodetector 97, respectively, to provide a fit for these elements sufficiently tight to maintain the elements in alignment.

Form members 90 and 91 define inwardly-concave surfaces 98 and 99, respectively, between which tubing 16 is held when the form elements 90 and 91 are in their closed position, as shown in FIG. 4. The curvature of these surfaces is dimensioned to correspond closely to the natural or unstressed curvature of the outside surface of tubing 16 so that when engaged to form members the tubing lumen is maintained in its unstressed cross-sectional shape notwithstanding pressure changes in the fluid contained therein.

To remove the tubing, it is merely necessary to separate form members 90 and 91. In metering apparatus 10 this is accomplished automatically upon the operator actuating lever 55 to open metering station 15, since form member 90 is mounted to a stationary housing member, and form member 91 is mounted to the movable pressure plate 50.

Figure 5A:
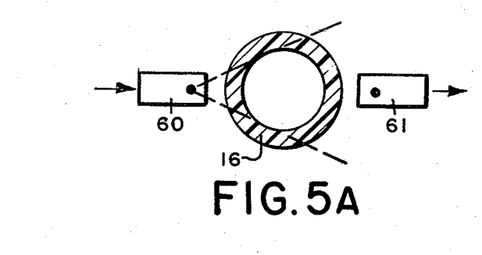
FIG. 5a is a diagrammatic depiction of the flow monitoring head of the metering apparatus in the absence of fluid in the lumen of the monitored tubing.
Figure 5B:
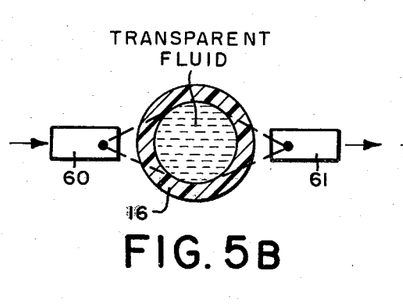
FIG. 5b is a diagrammatic depiction similar to FIG. 5a showing the flow monitoring head with clear fluid present.
Figure 5C:
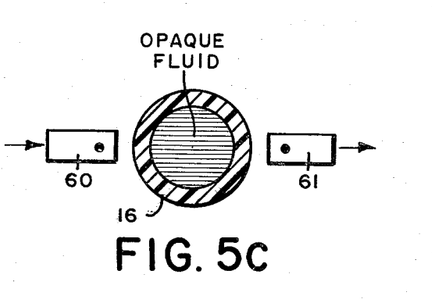
FIG. 5c is a diagrammatic depiction similar to FIG. 5a showing the slow monitoring head with opaque fluid present.

Referring to FIGS. 5A-5C, operation of the flow monitoring head is dependent on a focusing or lens effect produced by fluid in the lumen of the tubing. As shown in FIG. 5A, in the absence of fluid light from light source 60 diverges as it passes through the transparent walls of the tubing. As a result, only a small portion of the light transmitted through the tubing actually falls upon light detector 61, and the resulting signal produced by that device is small. When transparent fluid is present in the lumen of the tubing, as shown in FIG. 5B, the circular cross-section of the fluid mass, as defined by the inner surface of the wall of the tubing, forms a lens which focuses the light on detector 61. As a result, a greater portion of the transmitted light is actually incident on the detector and the resulting clear fluid detector output signal is greater, exceeding a predetermined clear fluid operating level. When opaque fluid is present in the lumen of the tubing, as shown in FIG. 5C, substantially all light is blocked from detector 61 and the resulting opaque fluid detector output signal is substantially zero, falling below a predetermined opaque fluid operating level. By comparing the light detector output signals for the conditions shown in FIGS. 5A, 5B and 5C, the bubble detection system of the invention detects the occurrence of bubbles in the flow systems.

In addition to source 60 and detector 61, flow monitoring head 62 includes an additional light detector 100 arranged in a bore 101 at right angles to the optical path between source 60 and detector 61. A portion of the light output of source 60 is directed to detector 100 by means of a beam splitter 102 of conventional construction positioned between source 60 and the adjacent wall of tubing 16. As a result, the output signal from detector 100 is indicative of the light output of source 60.

Figure 6:
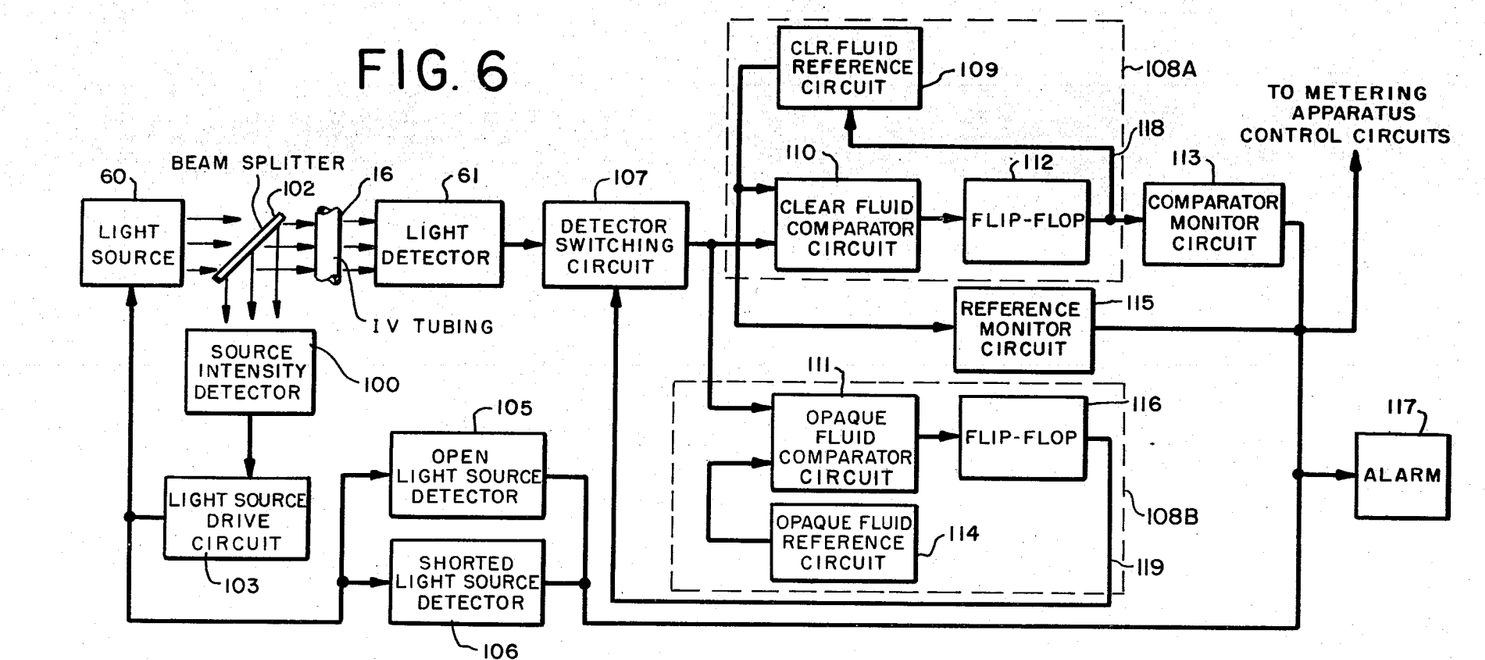
FIG. 6 is simplified functional block diagram of the bubble detection system of the invention.

In accordance with the invention, metering apparatus 10 includes a bubble detection system which operates in conjunction with light source 60 and light detectors 61 and 100 to terminate operation of the apparatus and sound an alarm upon occurrence of a bubble or fluid absence in either clear or opaque fluid in tubing 16. Referring to FIG. 6, a preferred embodiment of this detection system includes a light source drive circuit 103 for supplying operating power to light source 60. Within drive circuit 103, the output signal from source 60 intensity detector 100 is compared in a conventional manner with an applied reference signal to maintain the light output from light source 60 at a constant predetermined level.

Protection against open-circuit failure of light source 60 is provided by an open light source detector circuit 105 which continuously monitors the current supplied to the light source and provides an alarm output signal when the current falls below a predetermined minimum operating level. Similarly, protection against short-circuit failure of light source 60 is provided by a shorted light source detection circuit 106, which monitors the current supplied to the light source and provides an alarm output signal in the event that the current exceeds a predetermined maximum operating level. As will be seen presently, the alarm output signals from these monitoring circuits cause operation of the metering apparatus to be terminated and an alarm to be sounded.

The output signal developed by detector 61 is conveyed through detector switching means in the form of a detector switching circuit 107 to a first signal comparison means 108A which includes a clear fluid comparator circuit 110, and to a second signal comparison means 108B which includes an opaque fluid comparator circuit 111. In the first comparison means 108A the voltage level of the detector output signal is compared by comparator circuit 110 against a first predetermined reference voltage developed by a clear fluid reference circuit 109. This reference voltage is slightly less than the voltage level produced by the detector in the presence of a clear fluid, so that in the presence of clear fluid the applied detector output signal exceeds the applied reference voltage and the comparator circuit 110 produces an output signal. This output signal is applied to a flip-flop 112 with comparison means 108A.

Flip-flop, which may be a conventional clock-controlled reset-set (RS) type device, responds to the applied signal upon receipt of a clock pulse to produce a control signal on a line 118 which is applied to reference switching means in reference circuit 109 to cause the reference voltage produced by that circuit to be increased to a predetermined higher alternate level, setting on alternate comparison level for comparator circuit 110 which is attainable by light detector 61 only in the event of a short-circuit failure of the detector. Since in the absence of a short circuit this higher detector voltage level is not attained with clear fluid in tubing 16, an output signal is no longer produced by comparator circuit 110. This causes flip-flop 112 to revert to its original state upon receipt of the next clock pulse, and reference circuit 109 to in turn revert to its original state. As a result, the reference voltage applied to comparator circuit 110 is again at the first predetermined level, and a comparison is again effected by the comparator circuit. Thus, in the presence of clear fluid, and a corresponding clear fluid output signal from detector 61, comparator circuit 110, flip-flop 112 and reference circuit 109 alternate between states with application of clock pulses to the flip-flop. The periodic change in the control signal developed on line 118 by flip-flop 112 is monitored by a comparator monitor circuit 113, which acts only in the absence of such periodic changes in state to produce an alarm signal.

Should a bubble or other fluid absence occur in the clear fluid, the lack of lens effect in the flow detection station results in the detector output signal applied to comparator circuit 110 falling below the first clear fluid reference level established by reference circuit 109. As a result, comparator circuit 110 does not produce an output and flip-flop 112 does not change state. The lack of changes in state flip-flop 112 is detected by comparator monitor circuit 113, which responds by producing an alarm signal for application to an alarm circuit 117 and the metering apparatus control circuits.

To guard against a failure in reference circuit 109, a reference monitoring circuit 115 is provided to continuously monitor the reference voltage applied to comparator 110. In the event the applied reference voltage at any time falls below the clear fluid level, an onput signal is produced which results in operation of the metering apparatus being terminated and alarm 117 being sounded.

The output signal from light detector 61 is also compared within the second comparison means 108B against a second predetermined reference level established by an opaque fluid reference circuit 114 is opaque fluid comparator circuit 111. In the presence the detector output signal falls below this second reference level, which is slightly higher than the opaque fluid output level of detector 61, and comparator circuit 111 produces a clock-controlled output signal which is applied to an RS flip-flop 116. This causes flip-flop 116 to change state upon receipt of the next clock pulse, and in so doing to produce an inverting signal on a line 119 which causes detector switching circuit 107 to reverse the connections to light detector 61. As a result, the detector output signal is inverted, opaque fluid signals now exceeding the first predetermined clear fluid reference level, and clear fluid signals now falling below the second predetermined opaque fluid reference level. With the inverted detector output signal applied, opaque fluid comparator circuit 111 no longer produces an output and flip-flop 116 reverts to its original state upon receipt of the next clock pulse. This results in the detector output signal becoming non-inverted, comparator circuit 111 being reactivated, and the cycle repeating itself. Thus, in the presence of an opaque fluid, and a corresponding low level output signal from light detector 61, comparator circuit 111, flip-flop 116, and detector switching circuit 107 alternate between states, with application of each clock pulse to the flip-flop causing the output signal from light detector 61 to alternately be an unswitched low-level signal or a switched high level signal.

The inverted opaque fluid signal from detector 61, when applied to clear fluid comparator circuit 110 causes that stage to recognize a comparison and apply an output signal to flip-flop 112. Consequently, upon occurrence of the next clock pulse, comparator circuit 110 causes reference circuit 109 to apply a higher level shorted-sensor reference signal to comparator circuit 110. Since the detector is not shorted, and the detector output signal is no longer inverted by reason of flip flop 116 being clocked, the applied detector output signal is insufficient to effect a comparison and the output of comparator circuit 110 is terminated. This causes flip-flop 112 to revert to its former state after the next clock period, causing reference circuit 109 to revert to its normal mode, and comparator circuit 110 to again recognize a comparison between the reference voltage and the inverted detector output signal brought about by clocking of flip-flop 116.

Thus, in the presence of an opaque fluid, a periodic change in state occurs in flip-flop 112 which prevents comparator monitor circuit 113 from producing an alarm signal.

In the event a bubble or fluid absence occurs in the opaque fluid, the detector output signal exceeds the opaque reference level, and comparator circuit 111 does not produce an output signal. As a result, flip-flop 116 is not switched by the next clock pulse, the output of detector 61 is not inverted, and only the non-inverted no-fluid detector signal is applied to clear fluid comparator circuit 110. Since this signal is below the clear fluid reference level, comparator 110 does not produce an output and flip-flop 112 does not change state, and comparator monitor circuit 113 produces an alarm output signal which sounds alarm 117 and terminates operation of the apparatus.

In the event light detector 61 fails, the output signal provided by that device will constitute either a continuous zero level signal (open-circuit failure), or a continuous high level signal (short-circuit failure). The zero level signal, when applied to opaque fluid comparator 111, results in the production of an output signal which causes detector switching circuit 107 to invert the detector output signal. However, since no output signal is being produced by the detector, the switched signal is also at essentially a zero level, and as a result comparator circuit 111 continues to recognize a comparison and continues to provide an output signal to flip-flop 116 and switching circuit 107. The resulting continuous zero level detector output signal is not recognized by the clear fluid comparator circuit 110, flip-flop 112 is therefore not activated, and comparator monitor circuit 113 produces an output alarm signal which sounds alarm 117 and terminates operation of the metering apparatus.

In the event of a short-circuit in light detector 61 resulting in the production of a continuous high level detector output signal, clear fluid comparator circuit 110 responds to the applied detector signal being greater than the reference signal applied from clear fluid reference circuit 109 to generate an output signal for application to flip-flop 112. The subsequent change in state of flip-flop 112 results in reference circuit 109 switching to an alternate high reference level. Since the applied short-circuit detector output signal exceeds this higher reference, comparator circuit 110 continues to produce an output signal, flip-flop 112 remains in its switched state, and comparator monitor circuit 113, not detecting changes in state, produces an alarm output signal which sounds alarm 117 and terminates operation of the metering apparatus.

Figure 7:
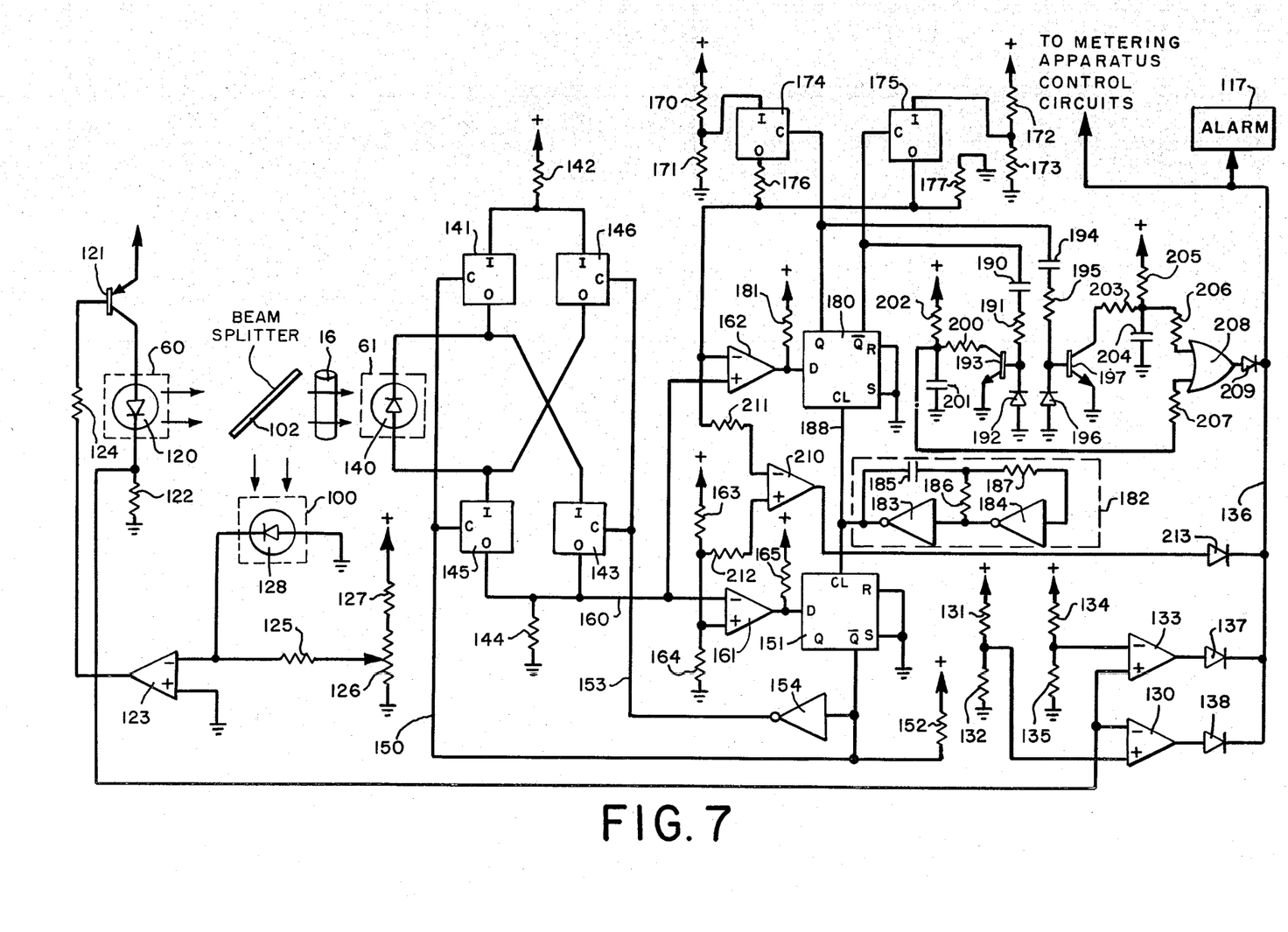
FIG. 7 is a simplified schematic diagram of a preferred circuit for the bubble detection system.

Referring to the simplified circuit diagram shown in FIG. 7, a light source 60 in the form of a light emitting diode 120 (LED) may be provided in the bubble detection a system of the invention. Unidirectional current is supplied to LED 120 by means of a series-connected transistor 121 and a series connected resistor 122. The conduction level of transistor 121, and hence the level of the light emitted by LED 120, is controlled by a differential amplifier 123 having its output connected to the base of the transistor through a resistor 124. The non-inverting input of amplifier 123 is connected to ground, and the inverting input is connected through a resistor 125 to the arm of a calibration adjust potentiometer 126. One end terminal is connected to ground and the other end terminal of potentiometer 126 is connected to a source of unidirectional current, so that the inverting input of amplifier 123 receives a reference signal having a voltage level dependent on the positioning of the potentiometer arm.

The light output of LED 120 is maintained at a constant level by a light source intensity detector 100 in the form of a photodetector 128 connected between the inverting input of amplifier 123 and ground. As the intensity of the light output from LED 120 increases, the voltage level at the inverting input of amplifier 123 decreases, causing conduction in transistor 121 to decrease. Thus, a closed-loop feedback network is established which functions to maintain the light output constant.

The level of current through LED 120 is reflected in the voltage developed across resistor 122. This voltage is applied to the inverting input of a first differential amplifier 130, which functions as part of the open-circuit light source detection circuit 106 to provide an alarm-initiating output signal in the event the applied current-indicating signal falls below a predetermined minimum level, as in the event of LED 120 becoming open. The predetermined minimum level is established by a reference signal applied to the non-inverting terminal of differential amplifier 130 by means of a voltage divider comprising resistors 131 and 132.

The voltage developed across resistor 122 is simultaneously applied to the non-inverting input of a second comparator 133 which functions as part of the short-circuit light source detection circuit 105 to provide an alarm-initiating output signal in the event the developed signal exceeds a predetermined maximum level, as in the event of LED 120 becoming shorted. To this end, a reference voltage is applied to the inverting terminal of comparator 133 by a voltage divider comprising resistors 134 and 135. The alarm-initiating output signals from comparators 130 and 133 are applied to an alarm bus 136 by means of forward-connected diodes 137 and 138. Thus, a signal is applied to the alarm bus in the event LED 120 becomes defective by either becoming open-circuited or short-circuited.

That portion of the light emitted by light source 120 which passes through tubing 16 impinges on a light detector 61 in the form of a photodiode 140. The cathode of this device is connected to a positive-polarity voltage-regulated unidirectional current source through a first bistable switch device 141 and series-connected resistor 142, and to ground through a second bistable switch device 143, and a resistor 144. The anode of photodiode 140 a connected to ground through a third bistable switch device 145 and resistor 144, and to the unidirectional current source of the system through a fourth bistable switch device 146 and resistor 142. Bistable switch devices 141, 143, 145 and 146 together function as switching circuit 107 (FIG. 6) to alternately reverse the connections to photodiode 140. The operating state of bistable switch devices 141 and 145 is controlled by a first switching control line 150 connected to the Q output of D-type flip-flop 151. A resistor 152 connected between this control line and a positive unidirectional current source provides required operating bias. The switching state of bistable switch devices 143 and 146 is controlled by a second switching control line 153 connected through an inverter amplifier 154 to control line 160. As a result of this arrangement, the operating state of the four bistable switching devices is determined by the switching state of flip-flop 151, with the switching states of devices 141 and 145 being at all times opposite to that of devices 143 and 146 as a result of inverter 154.

As is well known to the art, the level of current flow through photodiode 140 depends on the intensity of the light incident thereon. The level of current is sensed by resistor 144, which provides on a conductor 160 a detector output signal having a voltage level related to the intensity of the incident light. This detector output signal is applied to the inverting input of a first comparator amplifier 161, which comprises part of the opaque fluid comparator circuit 111 of the system, and to the non-inverting input of a second comparator amplifier 162, which comprises part of the clear fluid comparator circuit 110 of the system. A positive-polarity reference signal, providing a minimum opaque fluid threshold level for comparator 161, is applied to the non-inverting input of the comparator by a voltage divider comprising resistors 163 and 164.

The output of comparator 161 is connected to the delayed toggle (D) input of flip-flop 151. As a result, when the detector output signal supplied to the inverting input of comparator 161 falls below the reference level established by resistors 13 and 164, as in the presence of opaque fluid, upon occurrence of the subsequent clock pulse at the clock (CL) input of this device flip-flop 151 is caused to switch state, an bistable switching devices 141, 143, 145 and 146 are caused to switch the terminals of photodiode 140 to invert the detector output signal on conductor 160. As previously described, this results in the clear fluid comparator circuit 110 being activated to prevent an alarm from being sounded. A resistor 165 provides necessary operating bias for the output circuit of comparator 161.

The detector output signal 140 applied to the comparator 162 is compared with either a clear fluid reference signal applied to the inverting input of the comparator obtained from a first voltage divider comprising resistors 170 and 171, or a shorted detector reference signal obtained from a second voltage divider comprising resistors 172 and 173 series-connected between a source of positive-polarity unidirectional current and ground. The particular voltage divider providing reference voltage to comparator 162 is dependent on switching means in the form of first and second bistable switching devices 174 and 175, which comprise part of the clear fluid reference circuit 109. The output of switching device 175 is connected directly to the inverting terminal of the comparator, and the output of switching device 174 is connected through a resistor 176 to this terminal. A resistor 177 connected between the refernce voltage conductor and ground provides necessary operating bias.

The output of comparator 162 is applied to the delayed toggle (D) input of d-type flip-flop 180 having its Q and $\overline{Q}$ output terminals connected to respective control inputs of bilateral switching devices 174 and 175. As a result, at any one time either bistable switching device 174 or bistable switching device 175 is conductive, depending on the switching state of flip-flop 180. When flip-flop 180 is in its initial state, the Q output from that device applied to the control input of bistable switching device 174 results in that switching device applying of the clear fluid reference voltage from the first voltage divider comprising resistors 170 and 171 to the inverting input of the comparator. Conversely, when flip-flop 180 is in its transfer state, the $\overline{Q}$ output applied to the control input of bistable switching device 175 causes the shorted detector reference voltage established by the second voltage divider comprising resistors 172 and 173 to be applied to the comparator. A resistor 181 is provided at the output of comparator 162 to provide necessary operating bias.

In the presence of appropriate enabling signals from comparators 161 and 162 flip-flops 151 and 180 are caused to switch state by clock pulses applied to their clock (CL) input terminals. These clock pulses are generated by a continuously running oscillator circuit 182 comprising a pair of series-connected inverting amplifiers 183 and 184. In accordance with conventional practice, an RC timing circuit comprising a capacitor 185 and resistors 186 and 187 provides a feedback network causing the inverter amplifiers to oscillate at a predetermined frequency. The resulting output signal, which appears at the output of inverting amplifier 183, is applied through a conductor 188 to the clock inputs of flip-flops 151 and 180.

Changes in state of the Q and $\overline{Q}$ outputs of flip-flop 180 are sensed by comparator monitoring circuit 113, which comprises differentiating circuits associated with each output. A first differentiating circuit, comprising a capacitor 190, a resistor 191, a diode 192 and a transistor 193 is associated with the $\overline{Q}$ output. A second differentiating circuit comprising a capacitor 194, a resistor 195, a diode 196 and a transistor 197 is associated with the Q output. Transistor 193 has an associated output circuit comprising a resistor 200, a capacitor 201, and a resistor 202 which develops a first control voltage upon the occurrence of changes of output state at the $\overline{Q}$ output of flip-flop 180. Similarly, transistor 197 includes an output circuit comprising a resistor 203, a capacitor 204, and a resistor 205 for developing a second control voltage upon the occurrence of changes in output state at the Q output of flip-flop 180 bias. The control voltages developed across capacitors 201 and 204 are applied through respective isolation resistors 206 and 207 to respective inputs of an OR gate 208. The output of this gate, present whenever a control voltage is not present at either input, is applied through a forward-connected isolation diode 209 to the alarm-initiating bus 136. Thus, as long as flip-flop 180 continues to periodically change state, either as a result of the presence of a clear fluid, or as a result of the presence of an opaque fluid, no output signal is produced.

The reference signal applied to comparator 162 is monitored by means of a third comparator 210 having its inverting input connected to the inverting input of comparator 162 through an isolation resistor 211. A reference signal applied through a second isolation resistor 212 to the non-inverting input of the comparator establishes a reference level for the comparator such that an output signal is produced only in the event that the applied comparison voltage falls below the opaque fluid reference level normally applied to comparator 161. In the event that comparator 210 should detect an applied reference signal below the opaque fluid reference level, an output signal is produced which is applied to the alarm-initiating bus 136 through forward-biased isolation diode 213.

Clock circuit 182 provides clock pulses which synchronize the operation of flip-flops 151 and 180. Initially, comparator 162 is conditioned to sense the pressure of a clear fluid signal at the same time comparator 161 is conditioned to sense an opaque fluid signal. In the presence of an opaque fluid, comparator 161 senses a comparison and comparator 162 does not sense a comparison. Consequently, upon the subsequent clock pulse, the output of the detector is inverted and comparator 161 fails to sense a comparison and comparator 162 senses a comparison. Upon the next clock pulse, the detector output is again inverted, and comparator 161 senses a comparison, and comparator 162 does not.

Thus, a bubble detection system has been shown and described which is entirely automatic in operation and can be used with both opaque and clear fluids. While the system has been shown with discrete circuitry, it will be appreciated that all or a portion of the circuitry can be constructed in integrated form. Furthermore, while the bubble detection system of the invention is shown in conjunction with a peristaltic-type metering apparatus, it will be appreciated that the invention is equally useful in conjunction with other types of metering apparatus, including cassette-type apparatus. Since the system requires only a single light detector for detecting light passage through the tubing, it avoids the need for complex and expensive flow monitoring heads and may be retrofitted in existing metering apparatus where only a single detector is provided.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A bubble detector for detecting a fluid absence in either clear or opaque fluid in the transparent tubing of an administration set, said bubble detector comprising, in combination:

a light source arranged at one side of the tubing;
   a light detector generally arranged at the opposite side of the tubing for receiving light from said source having passed through the tubing, said detector being adapted to generate an output signal level indicative of the intensity of light incident on said detector, the level of said output being above a first predetermined level in the presence of a clear fluid in the tubing, and being below a second predetermined level which is lower than said first predetermined level in the presence of an opaque fluid within the tubing; and being between said first and second levels in the presence of a bubble or absence of fluid in the tubing, wherein said second level is selected so that when inverted it is higher than said first level;
   detector output switching means having an inverting signal input and a signal input connected to said detector output, said switching means being adapted to output said detector output signal in the absence of an inverting signal input and to output an inverted detector output signal in the presence of an inverting signal input,
   first and second comparision means connected to the output of said detector switching means, wherein said second comparison means is adapted to apply an inverting signal to said detector switching means in the event that said detector switching means output level falls below said second predetermined level, thereby causing said detector switching means to output an inverted detector output signal, and wherein said first comparision means is adapted to provide a control signal in the event that the detector switching means output level rises above said first predetermined level, and
   alarm circuit means adapted to issue an alarm in the event that said first comparision means fails to issue a control signal within a predetermined period of time.

2. A bubble detector as defined in claim 1 wherein said first comparison means include a first voltage comparator for producing an output signal upon said detector switching means output level rising above said first predetermined level, and a first flip-flop responsive to said first voltage comparator output signal for producing said control signal, and said second comparision means include a second voltage comparator for producing an output signal upon said detector switching means output level falling below said second predetermined level, and a second flip-flop responsive to said second voltage comparator output signal for producing said inverting signal, and wherein said detector includes a source of clock pulses for synchronizing the operation of said flip-flops.

3. A bubble detector as defined in claim 2 wherein said flip-flops are delayed-toggle type flip flops.

4. A bubble detector as defined in claim 1, further including additional light detector means for detecting the intensity of light emitted by said light source, and for providing an output signal indicative thereof, and light source supply means responsive to said intensity indicative output signal for supplying power to said light source so as to maintain a substantially constant light output level from said source.

5. A bubble detector as defined in claim 4 further including monitoring means for monitoring the power consumption of said light source and activating said alarm circuit means in the event said power consumption exceeds a predetermined maximum level or falls below a predetermined minimum level.

6. A bubble detector as defined in claim 1 wherein the level of said detector output is above a third predetermined level which is higher than said first predetermined level in the event that said detector short-circuits, and said first comparison means is adapted to further compare said detector switching means output with a reference voltage of said third predetermined level in response to said control signal, and being further adapted to maintain said control signal in the event that said detector switching output level exceeds said third level, and to remove said control signal in the event that said detector switching output level is below said third level, and wherein said alarm means is further adapted to issue an alarm in the event that said control signal is maintained for a predetermined period of time, thereby indicating a short-circuited detector.

7. A bubble detector for detecting a fluid absence in either clear or opaque fluid in the transparent tubing of an administration set, said bubble detector comprising, in combination:

a light source arranged at one side of the tubing;
a light detector generally arranged at the opposite side of the tubing for receiving light from said source having passed through the tubing, said detector being adapted to generate an output signal level indicative of the intensity of light incident on said detector, the level of said output being above a first predetermined level in the presence of a clear fluid in the tubing, and being below a second predetermined level which is lower than said first predetermined level in the presence of an opaque fluid within the tubing, and being above a third predetermined level which is higher than said first predetermined level in the event that said detector short-circuits, and being between said first and second levels in the presence of a bubble or absence of fluid in the tubing, wherein said second level is selected so that when inverted it is higher than said first level;
detector output switching means having an inverting signal input and a signal input connected to said detector output, said switching means being adapted to output said detector output signal in the absence of an inverting signal input and to output an inverted detector output signal in the presence of an inverting signal input,
first and second comparison means connected to the output of said detector switching means, wherein said second comparison means is adapted to apply an inverting signal to said detector switching means in the event that said detector switching means output level falls below said second predetermined level, thereby causing said detector switching means to output an inverted detector output signal, and wherein said first comparison means is adapted to compare said detector switching means output with a reference voltage of said first predetermined level to provide a control signal in the event that the detector switching means output level rises above said first predetermined level, and is adapted to further compare said detector switching means output with a reference voltage of said third predetermined level in response to said control signal, and to maintain said control signal in the event that said detector switching output level exceeds said third level, and to remove said control signal in the event that said detector switching output level in below said third level; and
alarm circuit means adapted to issue an alarm in the event that said control signal is maintained for a predetermined period of time.

8. A bubble detector as defined in claim 7 wherein said first comparison means include a first voltage comparator for producing an output signal upon said detector switching means output level rising above said first predetermined level, and a first flip-flop responsive to said first voltage comparator output signal for providing said control signal.

9. A bubble detector as defined in claim 8 wherein said second comparison means include a second voltage comparator for producing an output signal upon said detector switching means output level falling below said second predetermined level, and a second flip-flop responsive to said second voltage comparator output signal for providing said inverting signal.

10. A bubble detector as defined in claim 7 wherein said first comparison means include a first voltage comparator for producing an output signal upon said detector switching means output level rising above said first predetermined level, and a first flip-flop responsive to said first voltage comparator output signal for producing said control signal, and said second comparison means include a second voltage comparator for producing an output signal upon said detector switching means output level falling below said second predetermined level, and a second flip-flop responsive to said second voltage comparator output signal for producing said inverting signal, and said detector includes a source of clock pulses for synchronizing the operation of said flip-flops.

11. A bubble detector as defined in claim 10 wherein said flip-flops are delayed-toggle type flip flops.

12. A bubble detector as defined in claim 7 further including additional light detector means for detecting the intensity of light emitted by said light source, and for providing an output signal indicative thereof, and light source supply means responsive to said intensity indicative output signal for supplying power to said light source so as to maintain a substantially constant light output level from said source.

13. A bubble detector as defined in claim 12 further including monitoring means for monitoring the power consumption of said light source and activating said alarm circuit means in the event said power consumption exceeds a predetermined maximum level or falls below a predetermined minimum level.

14. A bubble detector for detecting a fluid absence in either clear or opaque fluid in the transparent tubing of an administration set, said bubble detector comprising, in combination:

- a light source arranged at one side of the tubing;
- a light detector generally arranged at the opposite side of the tubing for receiving light from said source having passed through the tubing, said detector being adapted to generate an output signal level indicative of the intensity of light incident on said detector, the level of said output being above a first predetermined level in the presence of a clear fluid in the tubing, and being below a second predetermined level which is lower than said first predetermined level in the presence of an opaque fluid within the tubing, and being above a third predetermined level which is higher than said first predetermined level in the event that said detector short-circuits, and being between said first and second levels in the presence of a bubble or absence of fluid in the tubing, wherein said second level is selected so that when inverted it is higher than said first level;
- detector output switching means having an inverting signal input and a signal input connected to said detector output, said switching means being adapted to output said detector output signal in the presence of an inverting signal input and to output an inverted detector output signal in the presence of an inverting signal input,
- first and second comparison means connected to the output of said detector switching means, wherein said second comparison means includes a voltage comparator and a delayed toggle flip-flop for applying an inverting signal to said detector switching means upon application of a clock pulse to the flip flop in the event that said detector switching means output level falls below said second predetermined level, thereby causing said detector switching means to output an inverted detector output level, and wherein said first comparison means includes a voltage comparator and a delayed toggle flip-flop for comparing said detector switching means output with a reference voltage of said first predetermined level to provide a control signal upon application of a clock pulse to the flip-flop in the event that the detector switching means output level rises above said first predetermined level, and is adapted to further compare said detector switching means output with a reference voltage of said third predetermined level in response to said control signal, and to maintain said control signal in the event that said detector switching output level exceeds said third level, and to remove said control signal in the event that said detector switching output level is below said third level;
- a source of clock pulses;
- means for applying said clock pulses to said flip-flops to provide synchronous toggling thereof; and
- alarm circuit means adapted to provide an alarm in the event that said control signal is maintained for a predetermined period of time.

15. A bubble detector as defined in claim 14 further including additional light detector means for detecting the intensity of light emitted by said light source, and for providing an output signal indicative thereof, and light source supply means responsive to said intensity indicative output signal for supplying power to said light source so as to maintain a substantially constant light output level from said source.

16. A bubble detector as defined in claim 15 further including monitoring means for monitoring the power consumption of said light source and activating said alarm circuit means in the event that said power consumption exceeds a predetermined maximum level or falls below a predetermined minimum level.

* * * * *